(12) United States Patent
Chandrasekaran et al.

(10) Patent No.: US 11,366,927 B1
(45) Date of Patent: Jun. 21, 2022

(54) COMPUTING SYSTEM FOR DE-IDENTIFYING PATIENT DATA

(71) Applicant: Allscripts Software, LLC, Raleigh, NC (US)

(72) Inventors: Sayee Balaji Chandrasekaran, Raleigh, NC (US); Jeremy Maxwell, Raleigh, NC (US)

(73) Assignee: Allscripts Software, LLC, Raleigh, NC (US)

( * ) Notice: Subject to any disclaimer, the term of this patent is extended or adjusted under 35 U.S.C. 154(b) by 215 days.

(21) Appl. No.: 16/558,291

(22) Filed: Sep. 2, 2019

Related U.S. Application Data (63) Continuation-in-part of application No. 14/102,522, filed on Dec. 11, 2013, now Pat. No. 10,403,392.

(51) Int. Cl.
*G06F 21/62* (2013.01)
*G16H 10/60* (2018.01)

(52) U.S. Cl.
CPC ......... *G06F 21/6245* (2013.01); *G16H 10/60* (2018.01)

(58) Field of Classification Search
CPC .............................. G06F 21/6245; G16H 10/60
See application file for complete search history.

(56) References Cited

U.S. PATENT DOCUMENTS

| | | | | |
|---|---|---|---|---|
| 8,275,850 B2 * | 9/2012 | Kohan | ............... | G16H 10/60 709/212 |
| 2005/0165623 A1 | 7/2005 | Landi et al. | | |
| 2006/0074983 A1 * | 4/2006 | Jones | ............... | G16H 10/65 |
| 2006/0129345 A1 | 6/2006 | Parvin et al. | | |
| 2006/0179075 A1 | 8/2006 | Fay | | |
| 2010/0306854 A1 | 12/2010 | Neergaard | | |
| 2011/0123118 A1 | 5/2011 | Nayar et al. | | |
| 2012/0041791 A1 * | 2/2012 | Gervais | ............... | G06F 21/6254 705/4 |
| 2012/0266254 A1 | 10/2012 | Gupta et al. | | |
| 2013/0080398 A1 | 3/2013 | Booth et al. | | |
| 2014/0280261 A1 | 9/2014 | Butler et al. | | |

FOREIGN PATENT DOCUMENTS

GB          1197429 A  *  7/1970  ......... G06F 16/9017

OTHER PUBLICATIONS

Campos-Outcalt, Doug. How does HIPAA affect public health reporting? Journal of Family Practice 53.9: 701(4). Dowden Health Media, Inc. (Sep. 2004)). (Year: 2004).*
"Non-Final Office Action for United States U.S. Appl. No. 14/102,522", dated Oct. 6, 2015, 14 pages.

(Continued)

*Primary Examiner* — Linh Giang Le
(74) *Attorney, Agent, or Firm* — Calfee, Halter & Griswold LLP (57) ABSTRACT

Described herein are various technologies pertaining to de-identifying patient data. A computing system removes protected health information and/or sensitive information from patient data by selectively replacing data in the patient data to retain the clinical relevance of the patient data after the patient data is de-identified, thereby retaining the utility of the de-identified patient data for tasks such as statistical analysis of patient data, testing of healthcare software functionality, and others.

20 Claims, 7 Drawing Sheets

(56) References Cited

OTHER PUBLICATIONS

"Response to the Non-Final Office Action for United States U.S. Appl. No. 14/102,522", Filed Date: Feb. 8, 2016, 18 pages.
"Final Office Action for United States U.S. Appl. No. 14/102,522", dated May 11, 2016, 19 pages.
"Response to the Final Office Action for United States U.S. Appl. No. 14/102,522", Filed Date; Sep. 12, 2016, 14 pages.
"Non-Final Office Action for United States U.S. Appl. No. 14/102,522", dated Apr. 17, 2017, 22 pages.
"Response to the Non-Final Office Action for United States U.S. Appl. No. 14/102,522", Filed Date: Oct. 17, 2017, 6 pages.
"Final Office Action for United States U.S. Appl. No. 14/102,522", dated Dec. 13, 2017, 22 pages.
"Response to the Final Office Action for United States U.S. Appl. No. 14/102,522", Filed Date: May 14, 2018, 17 pages.
"Non-Final Office Action for United States U.S. Appl. No. 14/102,522", dated Sep. 28, 2018, 13 pages.
"Response to the Non-Final Office Action for United States U.S. Appl. No. 14/102,522", Filed Date: Dec. 28, 2018, 19 pages.
"Notice of Allowance and Fees Due for United States U.S. Appl. No. 14/102,522", dated Apr. 23, 2019, 9 pages.

* cited by examiner

COMPUTING SYSTEM FOR DE-IDENTIFYING PATIENT DATA

RELATED APPLICATION

This application is a continuation in part of U.S. patent application Ser. No. 14/102,522, filed on Dec. 11, 2013, and entitled "DATA DE-IDENTIFICATION METHODOLOGIES". The entirety of this application is incorporated herein by reference.

BACKGROUND

De-identifying data is crucial in healthcare fields to protect patient privacy. Certain laws, such as the Health Insurance Portability and Accountability Act of 1996 (HIPAA), require that patient data of a patient be de-identified before the data can be transmitted to parties that are not authorized to view protected aspects of the patient data, such as a software developer that is to use the patient data to test the functionality of healthcare software. To test the functionality of the healthcare software, it is desirable that realistic clinical data is used. By using real clinical data collected from real patients instead of randomly generated data, the software developer is more likely to be able to verify the intended functionality of the healthcare software, which is done to ensure patient safety.

HIPAA defines protected health information (PHI) as information, including demographic information, in a medical record or designated record set that can be used to identify an individual and that was created, used, or disclosed in the course of providing a health care service such as diagnosis or treatment. PHI includes many common identifiers for individuals, including names, addresses, dates of birth, social security numbers, etc.

Conventional computer-implemented de-identifying techniques have been developed to alter PHI of a patient such that an identity of the patient cannot be readily determined from the altered PHI. However, there are various deficiencies associated with conventional computer-implemented de-identifying techniques. First, conventional computer-implemented de-identifying techniques were developed before the advent of large-scale analytics and therefore existing de-identifying techniques no longer sufficiently de-identify patient data. Large-scale analytics can be used to identify, to a reasonably high probability, a patient identity when provided with data that has been de-identified through us of these conventional techniques.

Conventional de-identifying techniques also tend not to be well-suited for maintaining the clinical relevance of a patient record while de-identifying the data. Rather, conventional de-identifying techniques generally randomize the PHI. Hence, conventional de-identifying techniques can produce de-identified data that is not well-suited for use in testing functionality of healthcare software (particularly clinical decision support functionality), as the produced de-identified data is not representative of clinically relevant patient data. This is due to the fact that conventional de-identifying techniques were not developed to ensure that a de-identified patient record retains clinical meaning with regard to itself and related patient records. For example, conventional de-identifying techniques might change the date field of a birth of a patient's child to occur prior to the patient's pregnancy. In another example, a conventional de-identifying technique might change the last names in patient records for siblings to two different last names, thereby losing an indication that the patients are related.

Additionally, conventional de-identifying techniques tend to lack configurability options and hence are not well-suited for varying end-uses. Furthermore, conventional de-identifying techniques are generally unable to recognize patient records belonging to the same patient across disparate databases. Therefore, when de-identifying multiple records pertaining to a same patient, a conventional computing system for de-identifying patient data creates multiple de-identified patient records, one for each of the multiple records that pertain to the patient. These multiple de-identified patient records are not identifiable as belonging to same patient, and therefore clinical relevance of these de-identified records to one another by virtue of being representative of a same patient is lost by a conventional system for de-identifying patient data, restricting the ability to do interoperability testing across systems.

SUMMARY

The following is a brief summary of subject matter that is described in greater detail herein. This summary is not intended to be limiting as to the scope of the claims.

Described herein are various technologies pertaining to de-identifying patient data. More specifically, a de-identifying application that is configured to de-identify patient data is described herein. The de-identifying application generates de-identified patient data by modifying or replacing protected health information (PHI) and/or other sensitive information in patient data using various de-identifying techniques. In operation, a computing system that executes the de-identifying application receives a request to de-identify data pertaining to a patient. In exemplary embodiments, the computing system may be or be included in a cloud platform and the de-identifying application may execute in a virtual machine that runs on the cloud platform. The de-identifying application processes patient data of the patient based upon configuration data that is used to configure functionality of the de-identification application. By way of example, the de-identifying application can be configured to de-identify patient data of different PHI categories differently. For instance, when de-identifying an address, a street number and street name may be transformed, while the city remains unchanged. In another example, a date in the patient data may be de-identified by transforming a date and a month, while the year remains unchanged. In yet another example, a first name and a last name of a first patient is transformed and instances of the same last name appearing in a database are transformed to a same de-identified last name. Other methods of de-identification are also contemplated for other categories of patient data such as social security numbers, payor information, relatives, insurance, etc. The de-identifying application may then store the de-identified patient data. The de-identifying application (or another application) may then transmit the de-identified patient data to a computing device, whereupon the de-identified patient data may be utilized in healthcare software testing, clinical studies, incorporated into a statistical model, etc.

In various exemplary embodiments, the de-identifying application can be configured to standardize an address in the patient data prior to de-identifying the patient data such that instances of similar addresses that are representative of a same physical address (e.g., Main Street, Anytown, Ohio and Main St., Anytown, Ohio) are identified as being the same address and are standardized to a common format. After an address is subject to standardization such that the format conforms to a standard, the standardized address is subjected to a de-identification process, where, for example, a street name is changed from a first street name to a second street name. In an exemplary embodiment, each time the first street name occurs in patient data, the de-identification application alters the first street name to the second street name, thus ensuring that the relationship between two patients that share an address is preserved in the de-identified data set.

The above-described technologies present various advantages over conventional computer-implemented de-identifying techniques pertaining to de-identifying of patient data. First, unlike conventional techniques, the de-identifying application described above is well-suited for maintaining the clinical relevance of a patient record while de-identifying the data. Additionally, the de-identifying application is configurable to perform various types of de-identification operations and hence is well-suited for varying end-uses of the de-identified patient data. Furthermore, the de-identifying application is able to identify patient records belonging to the same patient across disparate databases. In an exemplary embodiment, the de-identifying application de-identifies multiple patient records pertaining to a same patient by creating a single de-identified patient record that is representative of all of the multiple patient records. In another exemplary embodiment, the de-identifying application de-identifies multiple patient records pertaining to a same patient by creating multiple de-identified patient records that are indicated as pertaining to a same patient. By contrast, conventional computing systems for de-identifying patient data do not recognize when patient records belong to a same patient, and therefore create multiple de-identified records that are not identifiable as pertaining to the same patient, restricting the ability to do interoperability testing. Finally, the de-identifying application does not require frequent user interaction with a graphical user interface (GUI) each time that patient data is de-identified, thereby enabling automation of electronic de-identification of patient data.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

DETAILED DESCRIPTION

Various technologies pertaining to de-identifying patient data are now described with reference to the drawings, wherein like reference numerals are used to refer to like elements throughout. In the following description, for purposes of explanation, numerous specific details are set forth in order to provide a thorough understanding of one or more aspects. It may be evident, however, that such aspect(s) may be practiced without these specific details. In other instances, well-known structures and devices are shown in block diagram form in order to facilitate describing one or more aspects. Further, it is to be understood that functionality that is described as being carried out by certain system components may be performed by multiple components. Similarly, for instance, a component may be configured to perform functionality that is described as being carried out by multiple components.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

Further, as used herein, the terms "component," "application," and "system" are intended to encompass computer-readable data storage that is configured with computer-executable instructions that cause certain functionality to be performed when executed by a processor. The computer-executable instructions may include a routine, a function, or the like. It is also to be understood that a component or system may be localized on a single device or distributed across several devices. Further, as used herein, the term "exemplary" is intended to mean serving as an illustration or example of something, and is not intended to indicate a preference.

As used herein, the term "protected health information" (PHI) refers to information, including demographic information, in a medical record or designated record set that can be used to identify an individual and that was created, used, or disclosed in the course of providing a health care service such as diagnosis or treatment. PHI of patients may include, but are not limited to, personally identifying information such as names, geographic divisions (e.g., street address, city, county, precinct, ZIP code, equivalent geocodes of the foregoing, etc.), dates (including birth dates, admission dates, discharge dates, and death dates), telephone numbers, vehicle identifiers and serial numbers (including license plate numbers, vehicle identification numbers (VINs), and the like), email addresses, web uniform resource locators (URLs), social security numbers, Internet Protocol (IP) addresses, medical record numbers, biometric identifiers, including finger and voice prints, health plan beneficiary numbers, full-face photographs and any comparable images, account numbers, and certificate/license numbers. PHI may also include other unique identifying numbers, characteristics, and codes.

As used herein, the term "sensitive information" refers to information that is not PHI, but that is nonetheless desirable to exclude from the patient data (e.g., to reduce the probability that an identity of a patient to which the patient data pertains can be determined). For example, sensitive information could include the fact that a particular patient suffered a shark bite, as shark bites are rare enough to be potentially identifying of the patient.

As used herein, the terms "de-identify patient data," "de-identifying patient data," and the like refer to the process of modifying data entries that include PHI or sensitive data within the patient data with altered data entries resulting in the data entries no longer constituting PHI.

Figure 1:
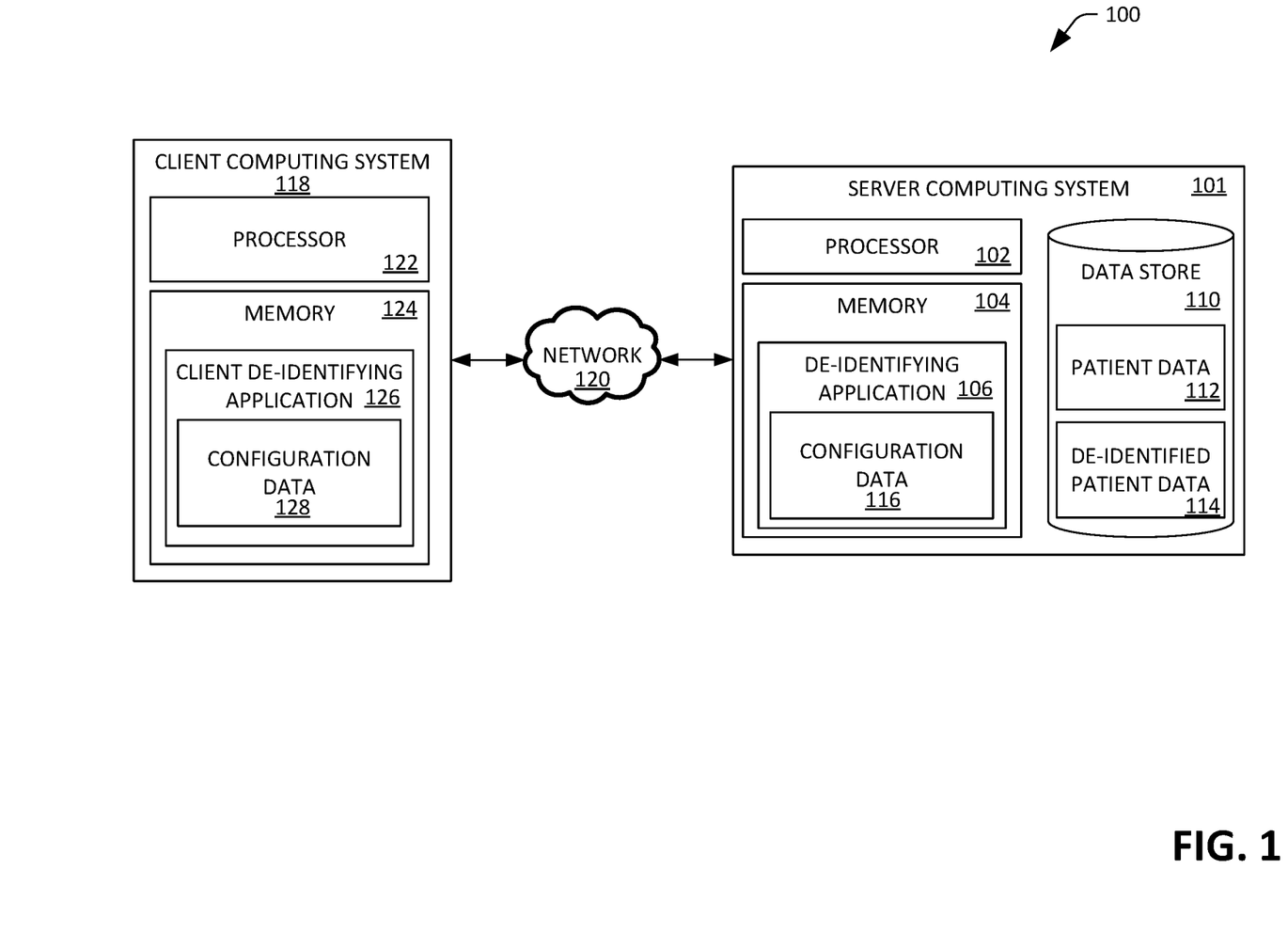
FIG. 1 is a functional block diagram of an exemplary computing system that facilitates de-identifying patient data.

With reference to FIG. 1, an exemplary computing environment 100 is illustrated, wherein the computing environment 100 includes an exemplary server computing system 101 that facilitates de-identifying patient data. The server computing system 101 includes a processor 102 and a memory 104, wherein the memory 104 has a de-identifying application 106 loaded therein. As will be described in greater detail below, the de-identifying application 106 (when executed by the processor 102) is generally configured to de-identify patient data to create de-identified patient data.

The server computing system 101 further includes a data store 110. The data store 110 includes patient data 112 pertaining to a patient. For example, the patient data 112 can be or include data that pertains to a patient and that has been generated by an electronic health records application (EHR). In another example, the patient data 112 can be or include data that pertains to a patient that was retrieved from a data warehouse, healthcare information exchange (HIE), or other repository of patient data. The data store 110 can further include de-identified patient data 114 (e.g., as generated by the de-identifying application 106 based upon patient data 112). The de-identifying application 106 is configured to generate the de-identified patient data 114 based upon the patient data 112.

In exemplary embodiments, the de-identifying application 106 can de-identify the patient data 112 based upon configuration data 116. By way of example, the configuration data 116 can indicate fields of data that are to be modified or replaced by the de-identifying application 106 in connection with de-identifying the patient data 112. In another example, the configuration data 116 can indicate whether a mapping entry is to be used to map original values in the patient data 112 to replacement values in the de-identified patient data 114, as described in greater detail below. The configuration data 116 can be data generated based upon user input received at the server computing system 101 or at another computing device. By way of example, the computing environment 100 further comprises a client computing system 118 that is in communication with the server computing system 101 via a network 120. The client computing system 118 comprises a processor 122 and memory 124, wherein the memory 124 has a client de-identifying application 126 loaded therein. The client de-identifying application 126, when executed by the processor 122, is configured to communicate with the de-identifying application 106 and can be, for example, a web browser, a dedicated application, The client de-identifying application 126 may receive input from a user (e.g., as received by way of a GUI of the client de-identifying application 126), wherein the user input defines configuration data 128. The client de-identifying application can transmit the configuration data 128 to the de-identifying application 106 such that the configuration data 116 is or includes the configuration data 128.

In exemplary embodiments, the patient data 112 can include, but is not limited to, electronic health records, prescription records, claims data, patient/disease registries data, health surveys data, and/or clinical trials data. For instance, electronic health records include, but are not limited to including, administration and demographic information, diagnosis data, treatment data, vitals of the patient (e.g., weight, body mass index (BMI), height, etc.), identifiers of prescription drugs, identifiers of allergies, identifiers of pharmacies that dispensed prescription drugs, identifiers of laboratory tests, identifiers of vaccines, physiological monitoring data, hospitalization data, patient insurance data, etc.

Demographic information can include a first name, a middle name, and a last name of the patient, an ethnicity of the patient, a race of the patient, a gender of the patient, an address (e.g., a street name, a house number, a country, a state, and a zip code) of the patient, an email address of the patient, a telephone number of the patient, a birth date of the patient, a fax number of the patient, and/or a social security number of the patient. The demographic information can also include a vehicle identifier (e.g., a license plate number) of a vehicle belonging to the patient, a web uniform resource locator (URL), an Internet Protocol (IP) address, biometric identifiers (e.g., finger prints, voice prints, etc.), health plan beneficiary numbers, full-face photographs, account numbers of the patient, and medical record numbers of the patient.

Administration information includes hospital discharge data (e.g., reported to a government agency), admission dates, or the like. Claims data includes data relating to billable interactions, such as insurance claims, between the patient and a healthcare delivery system. The claims data can include data relating to inpatient interactions, outpatient interactions, pharmacy claims and/or enrollment of the patient in a patient record system. Patient/disease registries data can include data generated by clinical information systems that track data for certain chronic conditions, such as Alzheimer's Disease, cancer, diabetes, heart disease, asthma, etc. Health surveys data can include data from national surveys pertaining to common chronic conditions. Clinical trials data includes data generated during conduction of clinical trials.

The patient data 112 may also include codes for laboratory orders, patient complaints or symptoms, allergies of the patient, vitals of the patient, and/or encounters of the patient with a healthcare provider.

In an embodiment, the patient data 112 may be stored in a database that is retained in the data store 110. In the embodiment, the patient data 112 comprises stored entries defined by rows and columns of a table of the database. Each row may be assigned to a different patient and each column may be assigned to a different category of the patient data 112, at least a portion of which are PHI categories. In an example, the database may include a first column assigned to last names of patients and a second column assigned to dates of birth of the patients. A first entry located at a first row and the first column may include a last name for a first patient. A second entry located at a second row and second column may include a date of birth for a second patient.

As indicated above, the data store 110 also includes de-identified patient data 114 of the patient that is generated by the de-identifying application 106. The de-identified patient data 114 is similar to the patient data 112 in that the de-identified patient data 114 includes data that pertains to patients. However, the de-identified patient data 114 differs from the patient data 112 in that PHI and/or sensitive information pertaining to the patients represented by the patient data 112 has been replaced in the de-identified patient data such that it is statistically improbable that a patient may be identified from the de-identified patient data 114. In an embodiment, the de-identified patient data 114 may be stored in a database. Although the data store 110 is in some instances described as including patient data 112 and de-identified patient data 114 for a single patient, it is to be understood that the data store 108 may store patient data 112 and de-identified patient data 114 for many different patients.

The de-identifying application 106 can be configured to perform de-identification of patient data based upon the configuration data 116. The configuration data 116 may include an identifier for a database (or a database server) that includes the patient data 112 that is to be de-identified, access credentials for the database, identifiers for rows and columns that are to be de-identified within the database, identifiers for rows and columns that are to be decrypted within the database, a batch size of patient data that is to be de-identified, a timeout duration, etc. Further the configuration data 116 may also specify categories of patient data wherein each category indicates a different type of data. Based upon the configuration data 116, the de-identifying application 106 can de-identify data pertaining to each of the specified categories differently. In an example, a category of patient data comprises data entries used to identify ethnicity. In this example, data entries of the category of patient data in the patient data 112 may include "African American," "White," "Pacific Islander," etc. In another example, a category of patient data can be a street address. In connection with de-identifying the patient data 112, the de-identifying application 106 replaces a data entry in a category of the patient data 112 with a de-identified data entry comprising a different data entry for the same category of patient data. In a specific example, the de-identifying application 106 can replace a data entry for the ethnicity category of patient data with another data entry belonging to the ethnicity category (e.g., replacing "White" with "African American". Other exemplary categories of patient data include, but are not limited to, gender, geographic divisions (e.g., states, countries, etc.), addresses, birth dates, etc.

Operation of the server computing system 101 is now set forth. The server computing system 101 receives the patient data 112 from a source. In an example, the source may be an electronic health records application (EHR) that has generated the patient data 112. In another example, the source may be a data warehouse. In still another example the source may be an HIE. The server computing system 101 can then receive a request to de-identify the patient data 112. In an exemplary embodiment, the server computing system 101 receives the request to de-identify the patient data 112 from a client computing system 118 executing a client de-identifying application 126. In another exemplary embodiment, the server computing system 101 receives the request to de-identify the patient data 112 by way of user input received at the server computing system 101.

Responsive to receipt of the request at the server computing system 101, the de-identifying application 106 de-identifies the patient data 112 based upon the request. The de-identifying application 106 de-identifies the patient data 112 by selectively replacing PHI or sensitive information in the patient data 112 to generate the de-identified patient data 114. In exemplary embodiments, the de-identifying application 106 selectively replaces the PHI or sensitive information based upon the configuration data 116 (e.g., as received or generated by the server computing system 101 based upon the request to de-identify the patient data 112). In one example, the de-identifying application 106 replaces at least one data entry that corresponds to PHI or sensitive information for a patient in the patient data 112 with a second data entry to generate the de-identified patient data 114. Due to the second data entry being data that is not identifying with respect to the patient (e.g., the information represented in the data is not true with respect to the patient), the de-identified patient data 114 has a lower statistical probability of being usable to identify the patient than the patient data 112. In connection with de-identifying the patient data 112, the de-identifying application 106 can replace a plurality of data entries in the patient data 112 based upon criteria indicated in the configuration data 116. Several examples of methods for replacing data entries based on the configuration data 116 are set forth below.

Retaining the clinical relevance of the patient data 112 when de-identifying the patient data 112 is desirable to maintain the utility of the de-identified patient data 114 for use in testing functionality of healthcare software, particularly software for clinical decision support.

In an embodiment, the de-identifying application 106 replaces the day and month of each date appearing in the patient data 112 while retaining the year of the dates (e.g., in a date of birth, a date of death, a date a treatment was administered, etc.). In further embodiments, the de-identifying application 106 can be configured to maintain an order of dates indicated in the patient data 112 when de-identifying the patient data 112. By way of example, when altering a first date and a second date that is later in time than the first date in the patient data 112, the de-identifying application 106 can replace the first date and the second date with a third date and a fourth date, respectively, wherein the fourth date is later in time than the third date. In other configurations, the time elapsed between the first date and the second date can be preserved such that the third date and fourth date have the same amount of time elapsed between them as between the first date and the second date.

In other embodiments, the configuration data 116 can indicate that the sex of the patient should not be altered. Maintaining the correct sex of the patient from the patient data 112 to the de-identified patient data 14 can prevent instances of the de-identified patient data 114 showing a man having given birth or a female patient having her prostate removed.

Geographic location and corresponding environmental determinants of health associated with that geographic location can have profound impacts on a patient's health. For instance, living in a food desert can affect a patient's nutrition, living or working near an environmental hazard can affect a patient's pre-disposition to health conditions linked to environmental factors, etc. These factors can affect likely diagnoses and can affect the relative importance of other factors of a patient's health. Thus, retaining a link between a geographic location of a patient and that patient's patient data in the patient data 112 is desirable for retaining the clinical relevance of the de-identified patient data 114.

To ensure this geographic link is retained when de-identifying the patient data 112, in an exemplary embodiment, the de-identifying application 106 transforms a street address indicated in the patient data by replacing a street number and a street name indicated in the street address, but retaining the same city and/or zip code. In another embodiment, the de-identifying application 106 transforms a street address by replacing a street number, a street name, and a zip code. In this embodiment the original zip code can be replaced with a new and different zip code where the new zip code shares one or more features with the original zip code. By way of example, the new zip code can be selected such that the new zip code has a resident average income within a threshold difference from a resident average income of the original zip code. For example, if the patient's home address is located in an zip code with a low average family income, the patient is more likely to be living in a food desert with less access to healthy food options as compared to patients living in a zip code with a higher average family income. This can have an impact on the health and relevant diagnoses of the patient. To retain the clinical relevance of the de-identified patient data 114 with respect to environmental health determinants, the de-identifying application 106 can generate a replacement address in a similar geographic location and/or environment as the original address indicated in the original patient data 112. In embodiments wherein the de-identifying application 106 replaces the zip code of an address, the de-identifying application 106 can further be configured to replace the original street name, street number, city, and/or state of the address with different values that collectively define a valid address for the replacement zip code. By way of example, the replacement street number and street name can be selected to be a street number and street name that define an address that physically exists in the replacement zip code.

In various embodiments, the de-identifying application 106 can be configured to standardize addresses indicated in the patient data 112 to a uniform format prior to de-identifying the addresses. By way of example, the de-identifying application 106 can determine that two address data entries are representative of a same physical address even if not identically spelled or formatted. For instance, a first address data entry in the patient data 112 could be "1234 Main Street Apt. B" and a second address data entry in the patient data 112 could be "1234 Main St. Apartment B." The de-identifying application 106 can determine that the first address data entry and the second address data entry are representative of a same physical address. The de-identifying application 106 can then standardize the first address data entry and the second address data entry so that they are identical, according to a format that can be specified in the configuration data 116. By way of example, the de-identifying application 106 can modify the first address data entry and the second address data entry so that both entries are, as modified, "1234 Main Street Apartment B."

By standardizing addresses indicated in the patient data 112, the de-identifying application 106 can facilitate replacement of each incidence of an address in the patient data 112 with a same address in the de-identified patient data 114. Continuing the example above, once addresses in the patient data 112 that are representative of the same physical address as "1234 Main Street Apartment B" are standardized to the same format, the de-identifying application 106 can perform a find and replace operation to replace all instances of the standardized address to a same replacement address. This can preserve information indicative of potential environmental health determinants across multiple patient records in the patient data 112.

For example, if a patient lives in a location where the water supply is contaminated with lead, when the patient's address is de-identified the home address can be de-identified to a home address located in a geographic location with a lead contaminated water supply. Thus, the connection between diagnoses such as ADHD in an adolescent can still be linked to the environmental determinant (lead) in the de-identified patient data 114. This allows the de-identified patient data to be used in research and allows the research results to remain meaningful. In another example, if the patient's home address is located in an impoverished socio-economic zip code, the patient is likely living in a food desert with decreased access to healthy food options, which may lead to an increase in nutrient deficient health conditions. This can have an impact on the health and diagnoses of the patient. Therefore, to retain the environmental health determinants of the de-identified patient data 114, it is desirable to generate a de-identified home address in a similar geographic location and/or environment.

Familial relationships indicated in the patient data 112 may also be important to retain in the de-identified patient data 114 for use in testing the functionality of healthcare software such as clinical decision support software. For instance, if a mother smokes, the child is more likely to develop asthma. Retaining the familial link between the smoker mother and the child in the de-identified patient data 114 preserves the causal relationship of the smoking and an asthma diagnosis. This can facilitate testing the functionality of clinical decision support software in connection with the software identifying potential causes of disease. In another example, a patient may have a genetic pre-disposition to breast cancer. Therefore, retaining the familial link indicated in the patient data 112 can be useful for an end use of the de-identified patient data 114. For instance, the de-identified patient data 114 may be used to test the functionality of software wherein the software is designed to predict the likelihood that a patient will suffer from a genetic condition. If the familial linkage to a genetic pool with breast cancer is lost, the de-identified patient data 114 will likely be unsuitable to test the functionality of the software.

To preserve a familial linkage indicated in the patient data 112, in an embodiment, the de-identifying application 106 can be configured to de-identify the patient data 112 such that when a last name of a patient represented in the patient data 112 is the same as the last name of another patient represented in the patient data 112, the last names of the patients will be de-identified to the same last name. It is to be understood that as used herein, a last name is intended to refer to a family name that is generally shared by members of the same family, whether or not such information appears subsequent to another name in the patient data 112 or is labeled as a "last" name.

The de-identifying application 106 can replace last names included in the patient data 112 based upon a mapping between original last names in the patient data 112 and replacement last names in the de-identified patient data 114. By way of example, responsive to replacing a first last name of a first patient in the patient data 112 with a second last name, the de-identifying application 106 can create a mapping data entry that indicates that when the first last name (e.g., Smith) is encountered in the patient data 112, it is to be replaced with the second last name (e.g., Jones) in the de-identified patient data 114. Subsequently, when the de-identifying application 106 identifies a last name data entry in the patient data 112 of "Smith" the de-identifying application 106 replaces the last name data entry with "Jones" in the de-identified patient data 114.

In another embodiment, a record of a patient that is included in the patient data 112 can comprise a list of relatives of the patient, where such relatives may also be represented by a patient record in the patient data 112. In such an embodiment, the de-identifying application 106 can be configured to update the list of relatives with the de-identified names of each of the relatives on the list of relatives. Stated differently, the de-identifying application 106 replaces names of the relatives in the patient data 112 in connection with generating the de-identified patient data 114, and then updates the list of relatives in the de-identified patient data 114 according to the replacement names of the relatives used in the de-identified patient data 114. Accordingly, the de-identified patient data 114 can retain an indication of a relationship between patient records of the patient and patient records of the relatives indicated in the list of relatives.

In order to mitigate the possibility of re-identification of patients based upon the de-identified patient data 114 through the use of statistical attacks, the de-identifying application 106 can be configured to, in some instances, replace a same last name indicated in the patient data 112 with different last names in the de-identified patient data 114. By way of example, it may be known to an attacker that a particular percentage of patients represented in the patient data 112 have a particular last name (e.g., where the patient data 112 is representative of patients in a known geographic area). In embodiments wherein the de-identifying application 106 replaces patient names in the patient data 112 with replacement patient names in the de-identified patient data 114 based upon a mapping, the de-identifying application 106 can be configured to use a mapping entry to map an original patient name to a replacement patient name only a pre-defined threshold number of times (e.g., 25 times, 50 times, or 100 times) before generating an additional mapping entry for the original patient name. The additional mapping entry for the original patient name can map the original patient name to a second replacement name. The additional mapping entry can be used by the de-identifying application 106 to replace instances of the original patient name with the second replacement name after the pre-defined threshold number of replacements of the original patient name with the first replacement name has occurred.

It is to be understood that the de-identifying application 106 can employ a mapping between original data entries in the patient data 112 and replacement data entries in the de-identified patient data 114 for any of various types of data. By way of example, the de-identifying application 106 can be configured to generate and maintain a mapping between original street names in the patient data 112 and replacement street names in the de-identified patient data 114.

It is understood that some or all of the patient data 112 may be encrypted. When the patient data 112 is encrypted, the de-identifying application 106 may decrypt the patient data 112 (or a portion thereof) using a cryptographic key that is accessible by the de-identifying application 106. When the patient data 112 is organized in a database, the de-identifying application 106 may determine whether a column in the database is to be decrypted based upon the configuration data 116 (e.g., whether the configuration data 116 indicates that data in that column is to be de-identified, such as when the column includes a particular type of patient data). The de-identifying application 106 decrypts the column when the configuration data 116 indicates that the column is to be decrypted. After decrypting all or a portion of the patient data 112, the de-identifying application 106 can proceed with de-identifying the patient data 112 as described in detail above. When de-identification is complete, the de-identifying application 106 can re-encrypt the patient data 112 and/or the de-identified patient data 114 to maintain the original data format.

In various embodiments, the de-identifying application 106 can be configured to delete the patient data 112 subsequent to performing de-identification of the patient data 112 to maintain the security of the patient data 112. The de-identifying application 106 can begin de-identifying the patient data 112 by loading at least a portion of the patient data 112 into the memory 104. The de-identifying application 106 then selectively replaces or modifies data included in the portion of the patient data 112 loaded in memory 104 to generate de-identified patient data. The de-identifying application 106 may then store the selectively modified portion of the patient data 112 in the data store 108 as the de-identified patient data 114. Subsequent to generating the de-identified patient data 114, the de-identifying application 106 may purge the patient data 112 from the data store 108 such that the patient data 112 is no longer retained in the data store 108. The de-identifying application 106 may also transmit the de-identified patient data 114 to the client computing system 118 by way of the network 120. The client computing system 118 may then use the de-identified patient data 114 for any of various end uses. For instance, the de-identified patient data 114 may be utilized in a clinical study. Alternatively, the de-identified patient data 114 may be utilized to test medical software applications.

Although the above-described process is described as de-identifying patient data for a single patient, it is to be understood that the de-identifying application 106 may de-identify patient data for many different patients. For instance, the server computing system 101 may de-identify patient data that pertains to multiple patients in the same batch of patient data 112 undergoing the de-identification process. Additionally, although the above-described technologies have been described as de-identifying patient data, it is to be understood that the above-described technologies may also be used to de-identify other types of data (i.e., data that is not patient data).

Figure 2:
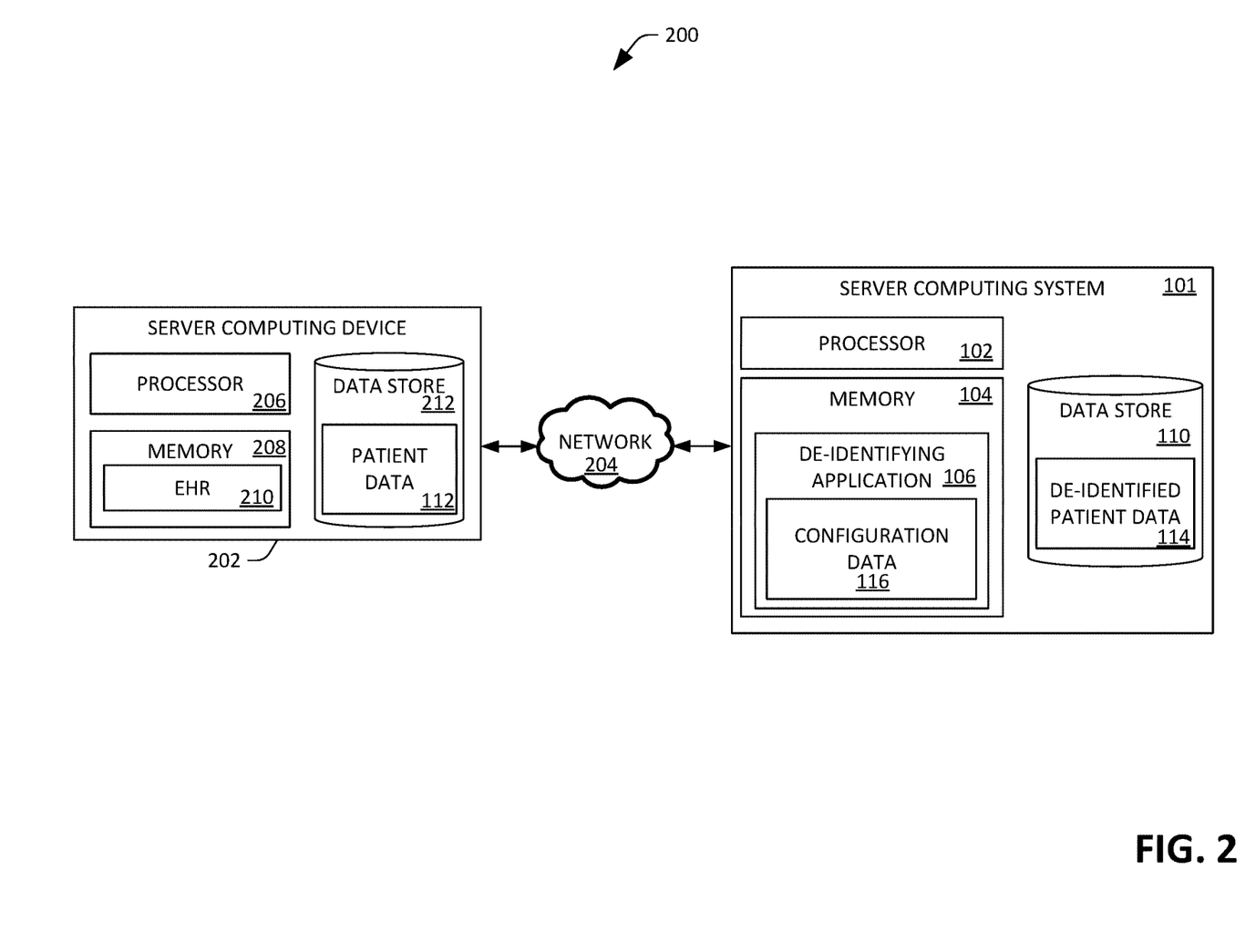
FIG. 2 is a functional block diagram of an exemplary computing environment that facilitates de-identifying patient data.

Turning now to FIG. 2, an exemplary computing environment 200 that facilitates de-identifying patient data is illustrated. The computing environment 200 includes the server computing system 101 and its various components (e.g., the processor 102, the memory 104, the de-identifying application 106, etc.) described above in the description of FIG. 1. In the computing environment 200, the server computing system 101 is not configured to retain the patient data 112 in the data store 110. Rather, the patient data 112 is received from an EHR and temporarily stored in the memory 104.

The computing environment 200 further includes a server computing device 202 that is in communication with the server computing system 101 by way of a network 204 (e.g., the Internet, intranet, etc.). The server computing device 202 comprises a processor 206 and memory 208, wherein the memory 208 has an EHR 210 loaded therein. In general, the EHR 210 (when executed by the processor 206) is configured to assist healthcare workers with providing care to patients. The EHR 210 is configured to perform functionality pertaining to patient intake, patient billing, insurance billing, prescription generation, maintaining a record of patient care over time, etc. The EHR 210 is often used by healthcare workers at the point of care (i.e., at a time when the healthcare worker is providing care to a patient). For example, a healthcare worker may retrieve data from a patient record maintained by the EHR 210 to relatively quickly ascertain problems being experienced by the patient, medications currently being taken by the patient, and so forth. The server computing device 202 additionally includes a data store 212. The data store 212 stores the patient data 112 described above in the description of FIG. 1. The patient data 112 stored in the data store 212 can be or include data generated by the EHR 210 based upon input received by the EHR 210 from healthcare workers in connection with provision of care to one or more patients.

The computing environment 200 operates in a manner similar to that of the computing environment 100 described above. However, in the computing environment 200, the server computing system 101 receives the patient data 112 directly from the EHR 210, but does not store the patient data 112 in the data store 110. Instead, the server computing system 101 stores the patient data 112 temporarily in the memory 104. The server computing system 101 then de-identifies the patient data 112 as described above to generate the de-identified patient data 114. Upon generating the de-identified patient data 114, the server computing system 101 in the computing environment 200 can delete the patient data 112 from the memory 104.

Although the de-identifying application 106 and the EHR 210 are depicted as being separate applications in the computing environment 200, in an embodiment, some or all of the functionality of the de-identifying application 106 may be incorporated directly into the EHR 210 such that the EHR 210 is able to generate the de-identified patient data 114 based upon the patient data 112.

Figure 3:
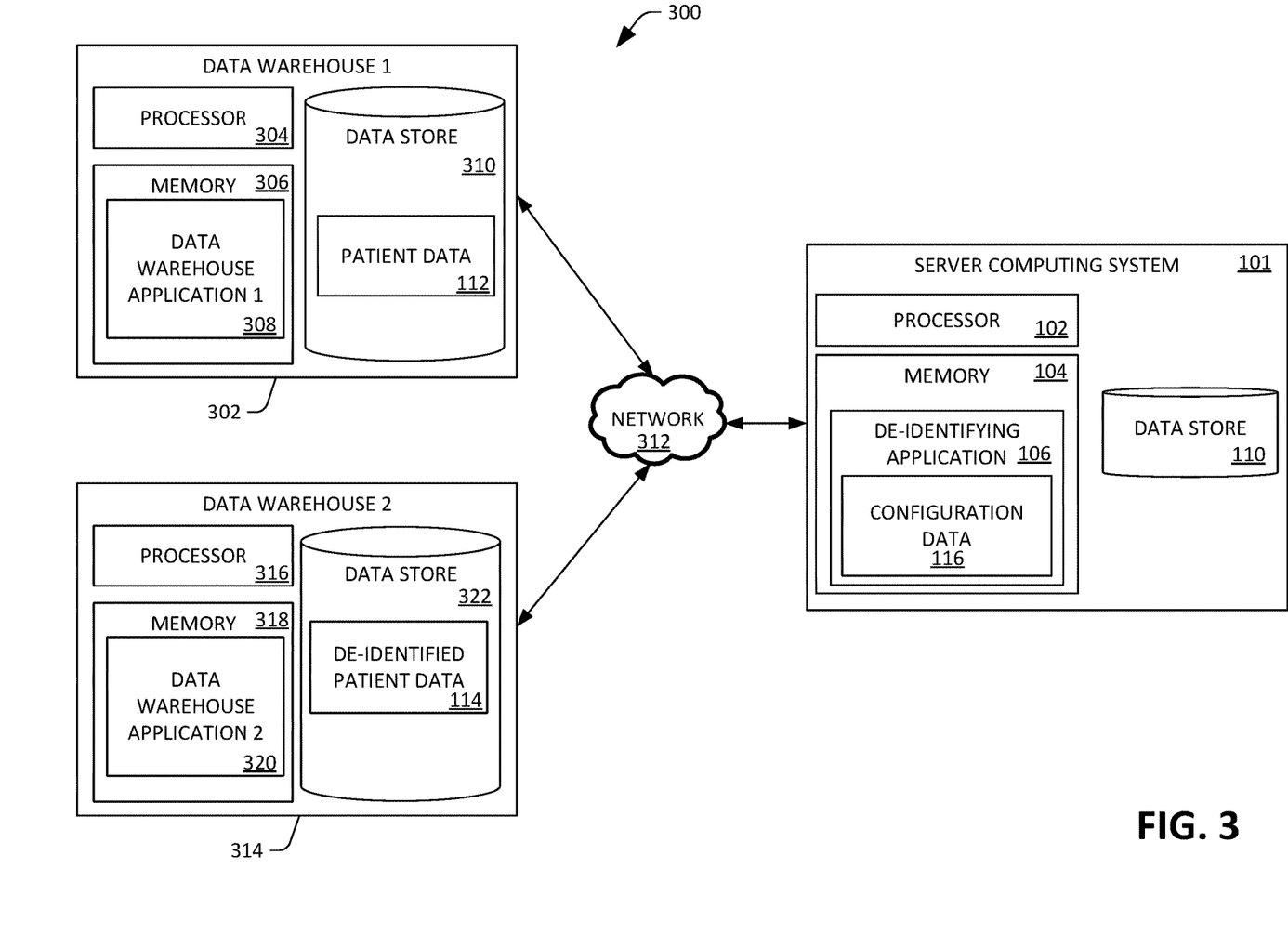
FIG. 3 is a functional block diagram of another exemplary computing environment that facilitates de-identifying patient data.

With reference now to FIG. 3, another exemplary computing environment 300 that facilitates de-identifying patient data is illustrated. The computing environment 300 includes the server computing system 101 and its respective components (e.g., the processor 102, the de-identifying application 106, etc.) described above in the description of FIG. 1. However, in the computing environment 300, the server computing system 101 does not retain the patient data 112 or the de-identified patient data 114 in the data store 110.

The computing environment 300 further includes a first data warehouse 302 that is in communication with the server computing system 101 by way of a network 312 (e.g., the Internet, intranet, etc.). The first data warehouse 302 comprises a processor 304 and memory 306, wherein the memory 306 has a first data warehouse application 308 loaded therein. In general, the first data warehouse application 308 (when executed by the processor 304) is configured to manage storage and retrieval of data retained by the first data warehouse 302. The first data warehouse 302 further includes a data store 310 that stores the patient data 112 described above in the description of FIG. 1.

The computing environment 300 additionally includes a second data warehouse 314 that is in communication with the server computing system 101 by way of the network 312 (or another network). The second data warehouse 314 comprises a processor 316 and memory 318, wherein the memory 318 has a second data warehouse application 320 loaded therein. In general, the second data warehouse application 320 (when executed by the processor 316) is configured to manage storage and retrieval of data retained by the second data warehouse 314. The second data warehouse 314 further includes a data store 322 that stores de-identified patient data 114.

The computing environment 300 operates in a manner similar to that of the server computing system 101 described above in the description of FIG. 1. However, in the computing environment 300, the server computing system 101 receives the patient data 112 from the first data warehouse 302 and temporarily stores the patient data 112 in the memory 104. The server computing system 101 can receive the patient data 112 from the first data warehouse 302 in response to a request for the patient data 112 transmitted to the first data warehouse 302 by the server computing system 101. When the server computing system 101 has completed de-identifying the patient data 112 (i.e., the server computing system 101 has generated the de-identified patient data 114), the server computing system 101 may transmit the de-identified patient data 114 to the second data warehouse 314 (without storing the de-identified patient data 114 in the data store 110), whereupon the second data warehouse 314 may retain the de-identified patient data 114 in the data store 322.

Figure 4:
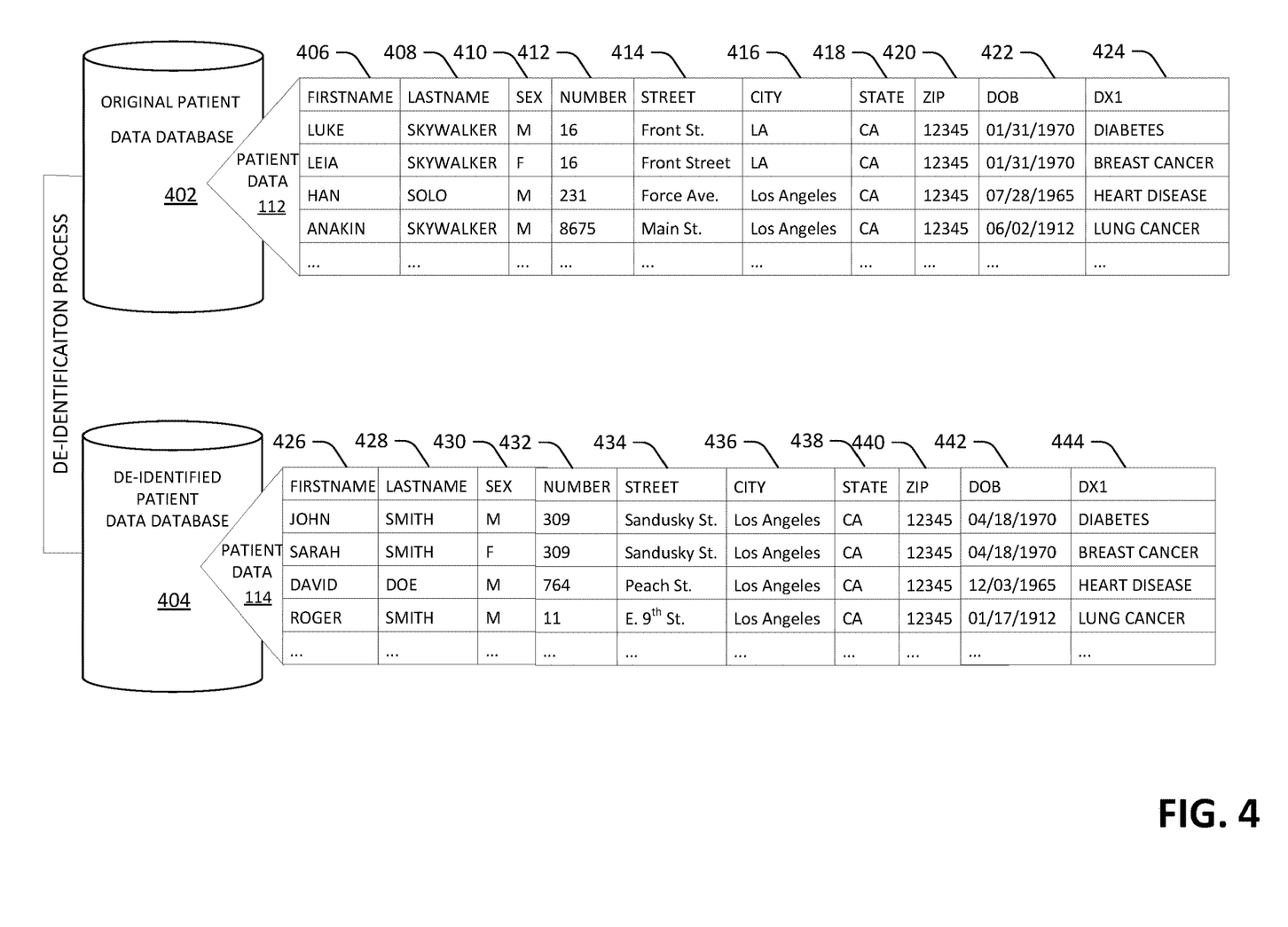
FIG. 4 is a schematic diagram that illustrates an exemplary patient data database and an exemplary de-identified patient data database.

With reference now to FIG. 4, an exemplary schematic illustrating the contents of a database storing the patient data 112 and a database storing the de-identified patient data 114 is shown. Specifically, an original patient data database 402 and a de-identified patient data database 404 are illustrated, which store the patient data 112 and the de-identified patient data 114, respectively. These databases 402, 404 may be housed in the data warehouses 302, 314 described above in regard to FIG. 3. Alternatively, the original patient data database 402 may be housed in the data store 212 while the de-identified patient data database 404 may be housed in the data store 110 of FIG. 2. In yet another embodiment, the original patient data database 402 and the de-identified patient data database 404 may both be housed in the data store 110 of FIG. 1.

The original patient data database 402 comprises patient data that is mapped to various categories of data. For purposes of illustration, the original patient data database 402 is illustrated in FIG. 4 with the following categories of data arranged in columns: first name 406, last name 408, sex 410, street number 412, street name 414, cite 416, state 418, zip code 420, date of birth 422, and diagnosis 1 424. The patient data 112 includes data in each of the categories 406-424 pertaining to a plurality of patients. It is to be understood that the patient data 112 can include substantially any number of categories corresponding to any of various types of patient data. In an exemplary embodiment, the patient data 112 includes categories of patient data as indicated in each respective patient's electronic health record (e.g., as generated by the EHR 210). The de-identified patient data database 404 comprises de-identified patient data 114 formed by the de-identification process performed by the de-identifying application 106 on the patient data 112 stored in the original patient data database 402. The de-identified patient data database 404 comprises the same categories of data included in the patient data 112 stored in the original patient data database 402: first name 426, last name 428, sex 430 house number 432, street name 434, city 436, state 438, zip code 440, date of birth 442, and diagnosis 1 444.

As indicated in FIG. 4, an embodiment of a de-identification process performed by the de-identifying application 106 de-identifies data included in the first name 406, last name 408, street number 412, street name 414, and date of birth 422 categories in the patient data 112. In the embodiment, the de-identifying application 106 identifies instances wherein patient records in the original patient data database 402 comprise the same last name in the last name category 408. For example, in the last name category 408, there are three instances of the last name "Skywalker" in the patient data 112. The de-identifying application 106 de-identifies the patient data 112 by replacing each instance of "Skywalker" with "Smith" in the last name 428 field of the de-identified patient data database 404 (e.g., based upon a mapping entry indicating a mapping from the name Skywalker to the name Smith, as described above).

In an embodiment, each address in the patient data 112 in the original patient data database 402 is broken down into five separate categories: street number, street name, city, state, and zip code. In other embodiments, addresses in the patient data 112 could be represented using additional categories such as county, parish, neighborhood, region (e.g., Piedmont, Appalachia, Pacific Northwest, American Southwest, etc.), or the like. Referring again to the original patient data database 402, each of the five address categories represented in the database 402 can then be de-identified by the de-identifying application 106 individually allowing further customization in de-identification method. For example, in the embodiment shown in FIG. 4, the de-identifying application 106 has de-identified the street number 412 and street name 414 contained in the original patient data database 402 with replacement values in the street number and street name categories 432, 434, however, the city 416, state 418, and zip code 420 has been retained during the de-identification process. This preserves the ability to take environmental and geographic healthcare determinants into consideration in analyses based upon the de-identified patient data 114. Although the city 416, state 418, and zip code 420 have not been replaced with de-identified values, the de-identifying application 106 has standardized each address such that each of the categories 432-440 in the de-identified patient data 114 relating to a patient address is in the same format using the same abbreviations.

In further embodiments, the de-identifying application 106 determines instances of duplicate addresses among the patient data 112 and retains the duplication in the de-identified patient data 114. The de-identifying application 106 can generally be configured to replace street numbers without performing a mapping from an original street number to a same replacement street number. Stated differently, the de-identifying application 106 generally replaces a same street number in multiple instances in the patient data 112 with different street numbers in the de-identified patient data 114. However, the de-identifying application 106 can be configured to replace an original street number with a same street number in instances where other parts of the original address are also the same. For instance, the address "16 Front St." appears in the first row of the patient data 112 in the original patient data database 402 and in the second row, albeit in unabbreviated form in the second instance. The de-identifying application 106 can replace the street number "16" in the address "16 Front St. LA, CA 12345" in the patient data 112 in the original patient data database 402 with "309" in both instances of the address, so that the first two rows of the de-identified patient data 114 in the de-identified patient data database 404 include the same address "309 Sandusky St. Los Angeles, Calif."

In an embodiment the de-identifying application 106 de-identifies data in the date of birth 422 category of the patient data 112 stored in the original patient data database 402 by replacing the month and date for each data entry in the date of birth 422 category while retaining the year. Accordingly, the de-identifying application 106 can be configured to selectively modify a portion of data within a data entry. The resulting de-identified data entries stored under the date of birth 442 category in the de-identified patient data database 404 comprise data entries wherein the month and date of the original patient data 112 have been replaced, but the year of the original patient data 112 has been left the same. In this way the de-identified patient data 114 is able to retain a timeline of patient data that makes clinical sense. For example, there will be no instances of the de-identified patient data 114 indicating that a three-year-old has given birth to three children.

It is to be understood that other ways of de-identifying patient data are contemplated as being within the scope of the present disclosure, and that the embodiments discussed with reference to FIG. 4 are for illustrative purposes and are not intended to be limiting as to the scope of the disclosure.

Figure 5:
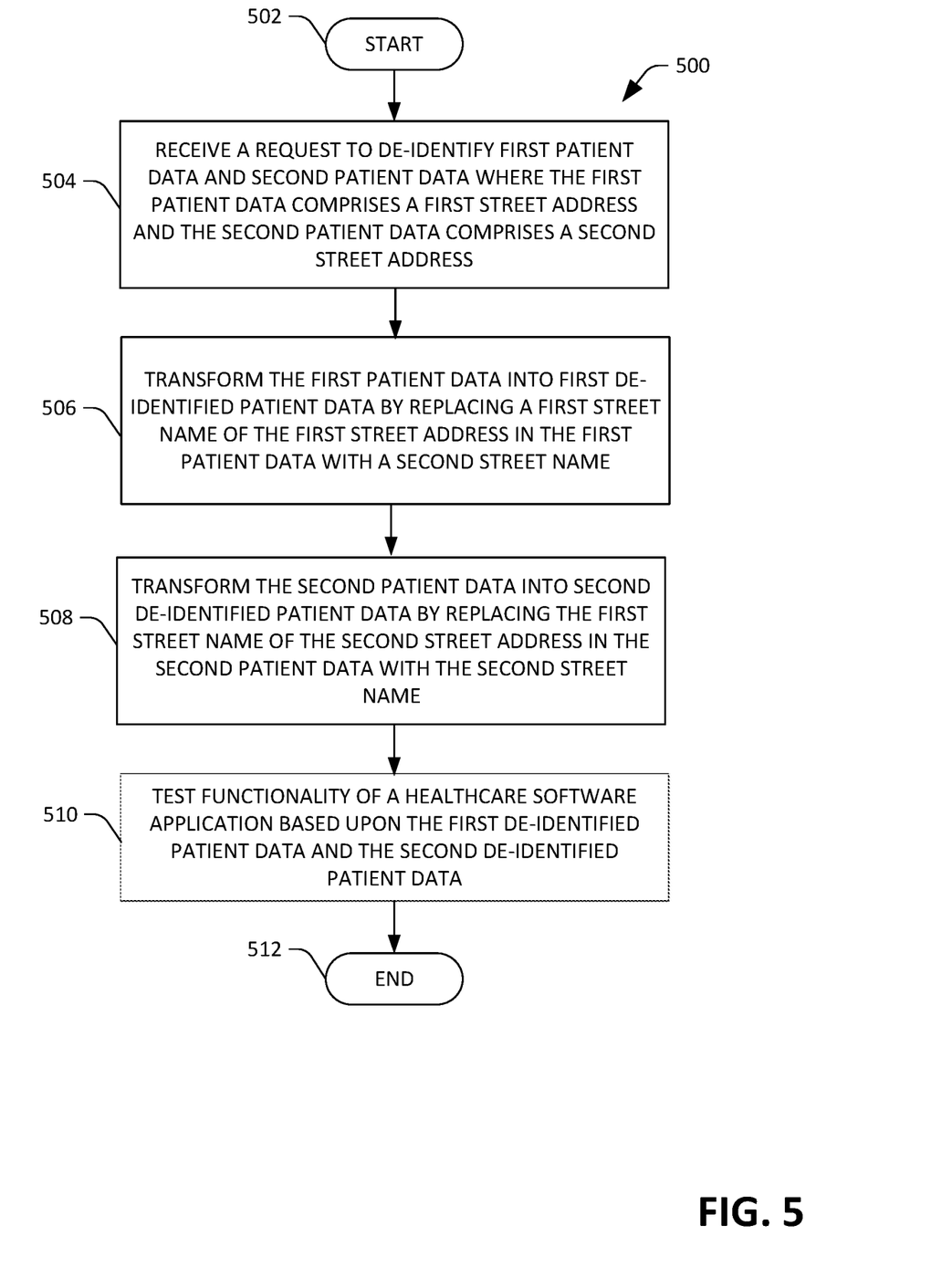
FIG. 5 is a flow diagram that illustrates an exemplary methodology performed by a computing system for de-identifying patient data.
Figure 6:
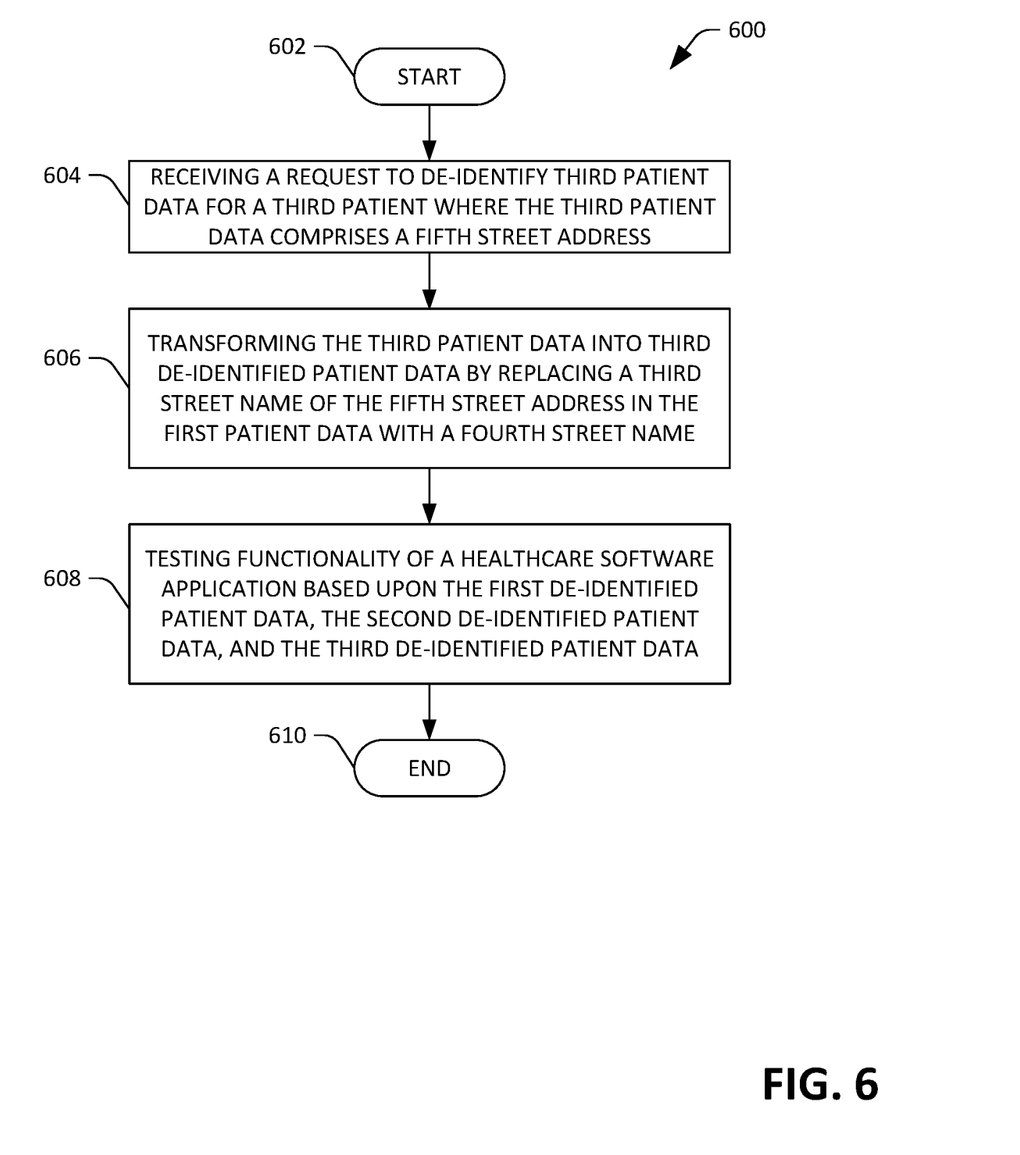
FIG. 6 is a flow diagram that illustrates another exemplary methodology performed by a computing system for de-identifying patient data.

FIGS. 5-6 illustrate exemplary methodologies relating to de-identifying patient data. While the methodologies are shown and described as being a series of acts that are performed in a sequence, it is to be understood and appreciated that the methodologies are not limited by the order of the sequence. For example, some acts can occur in a different order than what is described herein. In addition, an act can occur concurrently with another act. Further, in some instances, not all acts may be required to implement a methodology described herein.

Moreover, the acts described herein may be computer-executable instructions that can be implemented by one or more processors and/or stored on a computer-readable medium or media. The computer-executable instructions can include a routine, a sub-routine, programs, a thread of execution, and/or the like. Still further, results of acts of the methodologies can be stored in a computer-readable medium, displayed on a display device, and/or the like.

Referring now to FIG. 5, a methodology 500 performed by a computing system that facilitates de-identifying patient data is illustrated. The methodology 500 begins at 502, and at 504, the computing system receives a request to de-identify first patient data for a first patient and a second patient data for a second patient. The first patient data comprises a first street address and the second patient data comprises a second street address. The first and second street address both comprise a first street name. The request can include indicia of the first patient and the second patient. These indicia may be or include a social security number, medical record number (MRN), or the like. At 506, the computing system, based on the request, transforms the first patient data into first de-identified patient data. Transforming the first patient data into the first de-identified patient data comprises replacing the first street name in the first patient data with a second street name, resulting in the first de-identified patient data comprising a third street address that comprises the second street name. At 508, the computing system, based on the request, transforms the second patient data into second de-identified patient data. Transforming the second patient data into the second de-identified patient data comprises replacing the first street name in the second patient data with the second street name, resulting in the second de-identified patient data comprising a fourth street address that comprises the second street name. At 510, the first de-identified patient data and the second de-identified patient data are used to test the functionality of a healthcare software application. By using the first de-identified patient data and the second de-identified patient data for the software testing, the clinical relevance of a geographic relationship between the first and second addresses can be preserved, thereby preserving an environmental impact location that the shared street location of the addresses may have on the patient data and/or the functionality of the healthcare software application. For example, if the first patient and the second patient live in close proximity to contaminated ground water, the potential common environmental health impact of the first patient and the second patient having addresses on the same street is preserved in the de-identified patient data. Accordingly, the de-identified patient data can be used to test the ability of clinical decision support software to identify potential common environmental causes of a reported health concern when suggesting a diagnosis to a clinician. The methodology 500 concludes at 512.

Referring now to FIG. 6, a methodology 600 performed by a computing system that facilitates de-identifying patient data is illustrated. The methodology 600 begins at 602 where step 508 of the methodology 500 ends. At 604, the computing system receives a second request to de-identify third patient data for a third patient where the third patient data comprises a fifth street address. The fifth street address further includes a third street name. At 606, the computing system transforms the third patient data into third de-identified patient data. Transforming the third patient data into the third de-identified patient data comprises replacing the third street name in the third patient data with a fourth street name resulting in the third de-identified patient data comprising a sixth street address that comprises the fourth street name. At 608, the first de-identified patient data, the second de-identified patient data, and the third de-identified patient data are used to test the functionality of a healthcare software application. The methodology 600 concludes at 610.

Figure 7:
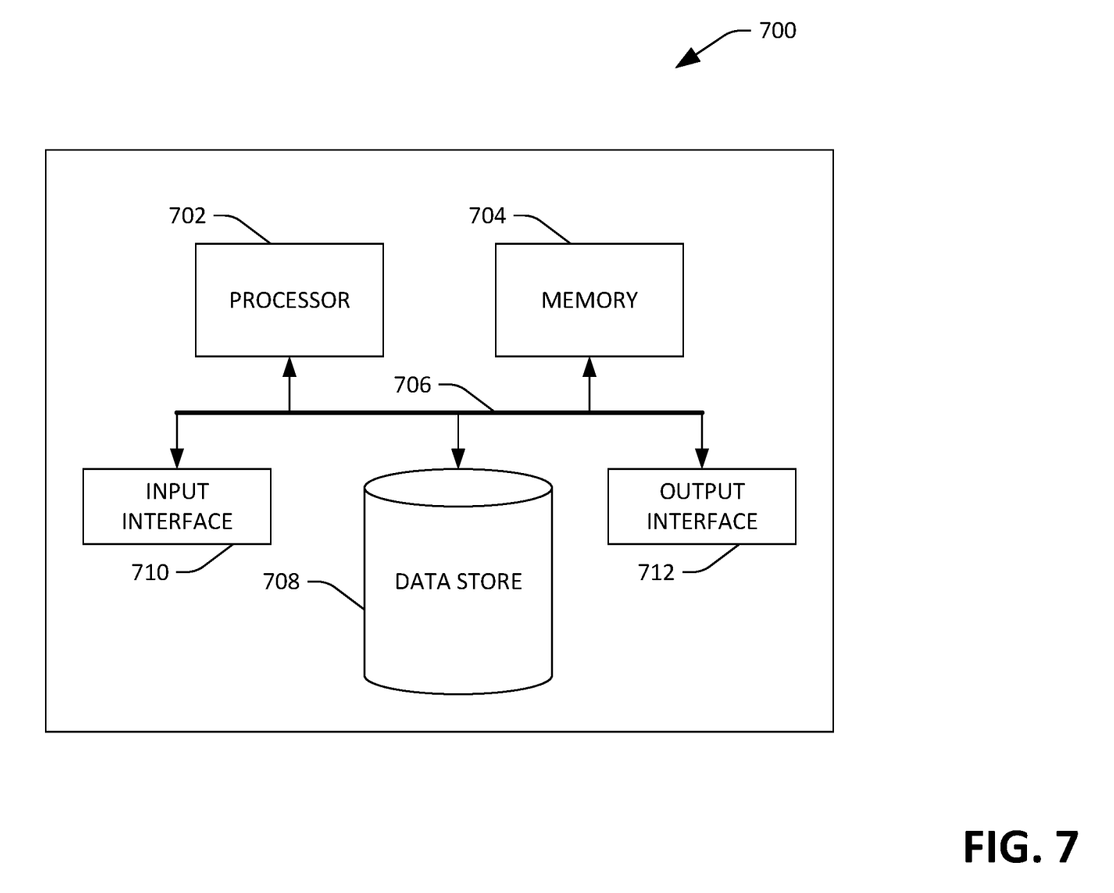
FIG. 7 is an exemplary computing system.

Referring now to FIG. 7, a high-level illustration of an exemplary computing device 700 that can be used in accordance with the systems and methodologies disclosed herein is illustrated. For instance, the computing device 700 may be used in a system that de-identifies patient data. By way of another example, the computing device 700 can be used in a system that receives instructions for de-identifying patient data in the form of configuration data. The computing device 700 includes at least one processor 702 that executes instructions that are stored in a memory 704. The instructions may be, for instance, instructions for implementing functionality described as being carried out by one or more components discussed above or instructions for implementing one or more of the methods described above. The processor 702 may access the memory 704 by way of a system bus 706. In addition to storing executable instructions, the memory 704 may also store patient data, de-identified patient data, configuration data, etc.

The computing device 700 additionally includes a data store 708 that is accessible by the processor 702 by way of the system bus 706. The data store 708 may include executable instructions, patient data, de-identified patient data, configuration data, etc. The computing device 700 also includes an input interface 710 that allows external devices to communicate with the computing device 700. For instance, the input interface 710 may be used to receive instructions from an external computer device, from a user, etc. The computing device 700 also includes an output interface 712 that interfaces the computing device 700 with one or more external devices. For example, the computing device 700 may display text, images, etc. by way of the output interface 712.

It is contemplated that the external devices that communicate with the computing device 700 via the input interface 710 and the output interface 712 can be included in an environment that provides substantially any type of user interface with which a user can interact. Examples of user interface types include graphical user interfaces, natural user interfaces, and so forth. For instance, a graphical user interface may accept input from a user employing input device(s) such as a keyboard, mouse, remote control, or the like and provide output on an output device such as a display. Further, a natural user interface may enable a user to interact with the computing device 700 in a manner free from constraints imposed by input devices such as keyboards, mice, remote controls, and the like. Rather, a natural user interface can rely on speech recognition, touch and stylus recognition, gesture recognition both on screen and adjacent to the screen, air gestures, head and eye tracking, voice and speech, vision, touch, gestures, machine intelligence, and so forth.

Additionally, while illustrated as a single system, it is to be understood that the computing device 700 may be a distributed system. Thus, for instance, several devices may be in communication by way of a network connection and may collectively perform tasks described as being performed by the computing device 700.

Various functions described herein can be implemented in hardware, software, or any combination thereof. If implemented in software, the functions can be stored on or transmitted over as one or more instructions or code on a computer-readable medium. Computer-readable media includes computer-readable storage media. A computer-readable storage media can be any available storage media that can be accessed by a computer. By way of example, and not limitation, such computer-readable storage media can comprise RAM, ROM, EEPROM, CD-ROM or other optical disk storage, magnetic disk storage or other magnetic storage devices, or any other medium that can be used to store desired program code in the form of instructions or data structures and that can be accessed by a computer. Disk and disc, as used herein, include compact disc (CD), laser disc, optical disc, digital versatile disc (DVD), floppy disk, and blu-ray disc (BD), where disks usually reproduce data magnetically and discs usually reproduce data optically with lasers. Further, a propagated signal is not included within the scope of computer-readable storage media. Computer-readable media also includes communication media including any medium that facilitates transfer of a computer program from one place to another. A connection, for instance, can be a communication medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio and microwave are included in the definition of communication medium. Combinations of the above should also be included within the scope of computer-readable media.

Alternatively, or in addition, the functionally described herein can be performed, at least in part, by one or more hardware logic components. For example, and without limitation, illustrative types of hardware logic components that can be used include Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs), etc.

What has been described above includes examples of one or more embodiments. It is, of course, not possible to describe every conceivable modification and alteration of the above devices or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. Furthermore, to the extent that the term "includes" is used in either the details description or the claims, such term is intended to be inclusive in a manner similar to the term "comprising" as "comprising" is interpreted when employed as a transitional word in a claim.

What is claimed is:

1. A computing system, comprising:
a processor; and
memory storing instructions that, when executed by the processor, cause the processor to perform acts comprising:
receiving an indication that a software application is to be tested based upon values in a de-identified database; and
responsive to receiving the indication, testing the software application based upon the values in the de-identified database, wherein the de-identified database is constructed based upon a database, wherein the de-identified database has a same format as the database such that fields in the database have corresponding fields in the de-identified database, and further wherein the database comprises:
a first row that includes first data for a first person, where the first data comprises a first street address of the first person, and further wherein the first street address includes a first street name;
a second row that includes second data for a second person, wherein the second data comprises a second street address of the second person, and further wherein the second street address includes the first street name, wherein a plurality of acts are undertaken to construct the de-identified database based upon the database, the plurality of acts comprising:
transforming the first data into first de-identified data, wherein transforming the first data into the first de-identified data comprises replacing the first street name in the first data with a second street name such that the first de-identified data comprises a third street address that comprises the second street name; and
transforming the second data into second de-identified data, wherein transforming the second data into the second de-identified data comprises replacing the first street name in the second data with the second street name such that the second de-identified data comprises a fourth street address that comprises the second street name, wherein the software application is tested
based upon the first de-identified data and the second de-identified data.

2. The computing system of claim 1, the acts further comprising:
prior to transforming the first data into the first de-identified data and transforming the second data into the second de-identified data, modifying the first street address and the second street address to conform to a standardized address format.

3. The computing system of claim 1, wherein the database further comprises a third row that includes third data for a third person, wherein the third data comprises a fifth street address of the patient, and further wherein:
the fifth street address includes a third street name, the plurality of acts further comprising:
transforming the third data into third de-identified data, wherein transforming the third data into the third de-identified data comprises replacing the third street name in the third data with a fourth street name such that the third de-identified data comprises a sixth street address that comprises the fourth street name.

4. The computing system of claim 1, wherein the first data comprises a first last name, wherein transforming the first data into the first de-identified data further comprises replacing the first last name with a second last name such that the first de-identified data comprises the second last name.

5. The computing system of claim 4, wherein the second data comprises the first last name, wherein transforming the second data into the second de-identified data further comprises replacing the first last name with the second last name such that the second de-identified data comprises the second last name.

6. The computing system of claim 1, wherein the first data comprises a first date of birth of the first person, the first date of birth comprising a first day, a first month, and a first year, and wherein transforming the first data into the first de-identified data further comprises replacing the first day in the first data with a second day and replacing the first month with a second month such that the first de-identified data comprises a second date of birth that comprises the second day, the second month, and the first year.

7. The computing system of claim 1, wherein the first street address further comprises a first street number and the second street address further comprises a second street number, wherein transforming the first data into the first de-identified data further comprises replacing the first street number with a third street number such that the third street address comprises the third street number, and wherein transforming the second data into the second de-identified data further comprises replacing the second street number with a fourth street number such that the fourth street address comprises the fourth street number.

8. A method executed by a processor of a computing system, the method comprising:
receiving an indication that a software application is to be tested based upon values in a de-identified database; and
responsive to receiving the indication, testing the software application based upon the values in the de-identified database, wherein the de-identified database is constructed based upon a database, wherein the de-identified database has a same format as the database such that fields in the database have corresponding fields in the de-identified database, and further wherein the database comprises:
a first row that includes first data for a first person, where the first data comprises a first street address of the first person, and further wherein the first street address includes a first street name;
a second row that includes second data for a second person, wherein the second data comprises a second street address of the second person, and further wherein the second street address also comprises the first street name, wherein a plurality of acts are undertaken to construct the de-identified database based upon the database, the plurality of acts comprising:
transforming the first data into first de-identified data, wherein transforming the first data into the first de-identified data comprises replacing the first street name in the first data with a second street name such that the first de-identified data comprises a third street address that comprises the second street name; and
transforming the second data into second de-identified data, wherein transforming the second data into the second de-identified data comprises replacing the first street name in the second data with the second street name such that the second de-identified data comprises a fourth street address that comprises the second street name, wherein the software is tested
based upon the first de-identified data and the second de-identified data.

9. The method of claim 8, further comprising:
prior to transforming the first data into the first de-identified data and transforming the second data into the second de-identified data, modifying at least one of the first street address or the second street address to conform to a standardized address format.

10. The method of claim 8, wherein the database further comprises a third row that includes third data for a third person, wherein the third data comprises a fifth street address of the patient, and further wherein:
the fifth street address comprises a third street name, the method further comprising:
transforming the third data into third de-identified data, wherein transforming the third data into the third de-identified data comprises replacing the third street name in the third data with a fourth street name such that the third de-identified data comprises a sixth street address that comprises the fourth street name.

11. The method of claim 8, wherein the first street address further comprises a first street number, the second street address further comprises the first street number, and the fifth street address further comprises the first street number, wherein transforming the first data into the first de-identified data further comprises replacing the first street number in the first data with a second street number such that the third street address comprises the second street number, wherein transforming the second data into the second de-identified data further comprises replacing the first street number in the second data with the second street number such that the fourth street address comprises the second street number, and wherein transforming the third data into the third de-identified data further comprises replacing the first street number in the third data with a third street number such that the sixth street address comprises the third street number.

12. The method of claim 8, wherein transforming the first data into the first de-identified data comprises replacing a first last name with a second last name such that the first de-identified data comprises the second last name.

13. The method of claim 12, wherein transforming the second data into the second de-identified data comprises replacing the first last name with the second last name such that the second de-identified data comprises the second last name.

14. The method of claim 13, wherein transforming the first data into the first de-identified data comprises replacing a first day, comprising a first date of death, in the first data with a second day and the first month with a second month such that the first de-identified data comprises a second date of death that comprises the second day, the second month, and the first year.

15. A non-transitory computer-readable storage medium comprising instruction that, when executed by a processor of a computing system, cause the processor to perform acts comprising:
receiving an indication that a software application is to be tested based upon values in a de-identified database; and
responsive to receiving the indication, testing the software application based upon the values in the de-identified database, wherein the de-identified database is constructed based upon a database, wherein the de-identified database has a same format as the database such that fields in the database have corresponding fields in the de-identified database, and further wherein the database comprises:
a first row that includes first data for a first person, wherein the first data comprises a first street address of the first person, and further wherein the first street address includes a first street name;
a second row that includes second data for a second person, wherein the second data comprises a second street address of the second person, wherein the second street address also comprises the first street name, wherein a plurality of acts are undertaken to construct the de-identified database based upon the database, the plurality of acts comprising:
transforming the first data into first de-identified data, wherein transforming the first data into the first de-identified data comprises replacing the first street name in the first data with a second street name such that the first de-identified data comprises a third street address that comprises the second street name; and
transforming the second data into second de-identified data, wherein transforming the second data into the second de-identified data comprises replacing the first street name in the second data with the second street name such that the second de-identified data comprises a fourth street address that comprises the second street name, wherein the software application is tested
based upon the first de-identified data and the second de-identified data.

16. The non-transitory computer-readable storage medium of claim 15, wherein the transforming the first data and the transforming the second data are based upon a mapping entry that indicates a mapping from the first street name to the second street name.

17. The non-transitory computer-readable storage medium of claim 16, wherein the transforming the first data and the transforming the second data are based upon the mapping entry indicating that the first street name has been replaced by the second street name in de-identified data less than a threshold number of times.

18. The non-transitory computer-readable storage medium of claim 15, wherein transforming the first data into the first de-identified data comprises replacing a first last name with a second last name such that the first de-identified data comprises the second last name.

19. The non-transitory computer-readable storage medium of claim 18, wherein transforming the second data into the second de-identified data comprises replacing the first last name with the second last name such that the second de-identified data comprises the second last name.

20. The non-transitory computer-readable storage medium of claim 19, wherein the transforming the first data and the transforming the second data are based upon a mapping entry indicating that the first last name is to be replaced with the second last name in de-identified data.

* * * * *